United States Patent [19]

Don Michael

[11] Patent Number: 5,460,610

[45] Date of Patent: Oct. 24, 1995

[54] TREATMENT OF OBSTRUCTIONS IN BODY PASSAGES

[76] Inventor: T. Anthony Don Michael, 4109 Sill Pl., Bakersfield, Calif. 93306

[21] Appl. No.: 140,528

[22] Filed: Oct. 25, 1993

Related U.S. Application Data

[63] Continuation-in-part of Ser. No. 868,961, Apr. 16, 1992, Pat. No. 5,306,249, which is a continuation-in-part of Ser. No. 808,924, Dec. 18, 1991, Pat. No. 5,222,941, which is a division of Ser. No. 492,582, Mar. 13, 1990, Pat. No. 5,090,960, which is a continuation-in-part of Ser. No. 464,029, Jan. 12, 1990, abandoned.

[51] Int. Cl.$^6$ .................................................. A61M 29/00
[52] U.S. Cl. ...................... 604/101; 604/264; 606/192
[58] Field of Search ......................... 604/96–103, 264, 604/280; 606/191–196

[56] References Cited

U.S. PATENT DOCUMENTS

| | | | |
|---|---|---|---|
| 3,978,863 | 9/1976 | Fettel et al. | 606/192 |
| 4,160,454 | 7/1979 | Foux | 604/93 |
| 4,351,342 | 9/1982 | Wiita et al. | 604/97 |
| 4,423,725 | 1/1984 | Boran et al. | 604/101 |
| 4,445,892 | 5/1984 | Hussein et al. | 604/101 |
| 4,512,348 | 4/1985 | Uchigaki et al. | 128/632 |
| 4,581,017 | 4/1986 | Sahota | 604/101 |
| 4,608,984 | 9/1986 | Fogarty | 606/194 |
| 4,610,662 | 9/1986 | Weikl | 604/101 |
| 4,636,195 | 1/1987 | Wolinsky | 604/101 |
| 4,693,243 | 9/1987 | Buras | 604/101 |
| 4,696,668 | 9/1987 | Wilcox | 604/101 |
| 4,705,503 | 11/1987 | Dorman et al. | 128/632 |
| 4,723,549 | 2/1988 | Wholey | 604/101 |
| 4,762,125 | 8/1988 | Leiman | 604/35 |
| 4,782,834 | 11/1988 | Maguire et al. | 606/194 |
| 4,798,586 | 1/1989 | Stevens | 604/96 |
| 4,824,436 | 4/1989 | Wolinsky | 604/53 |
| 4,857,045 | 8/1989 | Rydell | 604/22 |
| 4,944,745 | 7/1990 | Sogard et al. | 604/96 |
| 4,976,692 | 12/1990 | Alad | 604/101 |
| 4,983,167 | 1/1991 | Sahota | 604/96 |
| 5,000,734 | 3/1991 | Boissignac et al. | 604/96 |
| 5,020,537 | 6/1991 | Günther | 128/634 |
| 5,028,395 | 7/1991 | Sebille et al. | 128/634 |
| 5,047,208 | 9/1991 | Schweitzer et al. | 128/634 |
| 5,059,178 | 10/1991 | Ya | 604/101 |
| 5,078,135 | 1/1992 | Capnoli | 128/632 |
| 5,090,960 | 2/1992 | Don Michael | 604/101 |
| 5,097,834 | 3/1992 | Skrabal | 128/632 |
| 5,109,850 | 5/1992 | Blanco et al. | 128/635 |
| 5,135,484 | 4/1992 | Wright | 604/101 |
| 5,158,540 | 10/1992 | Wijay et al. | |
| 5,176,638 | 1/1993 | Don Michael | 604/101 |
| 5,222,941 | 6/1993 | Don Michael | 604/101 |
| 5,304,132 | 4/1994 | Jang | 604/96 |
| 5,306,249 | 4/1994 | Don Michael | 604/101 |
| 5,342,305 | 8/1994 | Shonk | 604/101 |
| 5,358,487 | 10/1994 | Miller | 604/96 |
| 5,415,635 | 5/1995 | Bagaoisan | 604/101 |

FOREIGN PATENT DOCUMENTS 8100676  3/1981  Germany ........................... 604/95

Primary Examiner—C. Fred Rosenbaum
Assistant Examiner—Chalin Smith
Attorney, Agent, or Firm—Spensley Horn Jubas & Lubitz

[57] ABSTRACT

A device for treating conditions causing obstructions in a body passage, composed of a catheter dimensioned to be insertable into the body passage and having a lateral wall and a distal end via which the catheter can be inserted into the body passage, the catheter being provided internally with fluid conducting passages and a fluid outlet passage which extends through the lateral wall and communicates with one of the fluid conducting passage; and first and second balloons carried by the catheter and extending outwardly from the lateral wall, the balloons communicating with respective fluid conducting passages and being disposed so that the first balloon is located between the fluid outlet passage and the distal end of the catheter, wherein one of the balloons is a high compliance volume balloon and the other of the balloons is a low compliance pressure balloon dimensioned to radially dilate the body when expanded by a fluid under pressure.

9 Claims, 2 Drawing Sheets

TREATMENT OF OBSTRUCTIONS IN BODY PASSAGES

This is a continuation-in-part of U.S. application Ser. No. 07/868,961, filed Apr. 16, 1992, now U.S. Pat. No. 5,306,249, which is a continuation-in-part of U.S. application Ser. No. 07/808,924, filed Dec. 18, 1991, now U.S. Pat. No. 5,222,941, which is a division of U.S. application Ser. No. 07/492,582, filed Mar. 13, 1990, now U.S. Pat. No. 5,090,960, itself a continuation-in-part of application Ser. No. 07/464,029, filed Jan. 12, 1990, now abandoned.

BACKGROUND OF THE INVENTION

The present invention relates to the treatment of obstructions or abnormal tissue, within body passages, particularly but not exclusively blood vessels.

The human body is composed of a variety of types of passages, including blood vessels, intestines, urinary passages, etc. which may be the site of abnormal growths or deposits which create obstructions. Since such obstructions interfere with normal body functioning, and can frequently be life threatening, considerable research has been devoted to techniques for removing them from the affected body passage.

For example, in the case of blood vessels, and particularly arteries, it is not uncommon for clots or plaque to form on the vessel wall and to grow to such an extent as to substantially impede, if not totally prevent, blood flow through the artery. Techniques which are in use, or have been proposed, for dealing with such obstructions include bypass surgery, angioplasty techniques, in which the vessel is mechanically dilated at the site of the obstruction in order to reopen the blood flow path, and a variety of techniques for mechanically removing the obstruction from the vessel wall. All of the techniques developed or proposed thus far have been found to possess one drawback or another.

Balloon angioplasty is frequently employed when an artery is partially blocked because it represents an essentially non-surgical technique for achieving an immediate opening of the blood flow path. In many cases, the portion of the artery which is subjected to balloon angioplasty will remain open for a substantial period of time. On the other hand, it is a quite common occurrence for a new blockage to develop in the location which has been subjected to balloon angioplasty. It appears that the new blockage occurs as a response of the blood vessel tissue to the mechanical damage resulting from the balloon angioplasty procedure. Specifically, balloon angioplasty will frequently, if not invariably, effect some tearing of the blood vessel wall and the ensuing healing process involves the development of smooth muscle tissue which tends to create a new blockage.

It is known that the materials which commonly form obstructions in blood vessels are capable of being dissolved by various chemical agents, but that such agents cannot be introduced into the circulatory system in a concentration sufficient to achieve an effective dissolution action. However, it has been recently proposed to confine such agents to the region of an obstruction in order to enable a sufficient concentration of the agent to be established in a medium which is in contact with the obstruction, without exposing the remainder of the circulatory system to the dissolution agent, or at least to unacceptably high concentrations of that agent. Such a technique is the subject, for example, U.S. Pat. No. 5,222,941.

SUMMARY OF THE INVENTION

It is an object of the present invention to provide a method and apparatus permitting blockages in blood vessels and other body passages to be eliminated in an improved manner.

The above and other objects are achieved, according to the present invention, by a device for treating conditions causing obstructions in a body passage, comprising: a catheter dimensioned to be insertable into the body passage and having a lateral wall and a distal end via which the catheter can be inserted into the body passage, the catheter being provided internally with fluid conducting passages and a fluid outlet passage which extends through the lateral wall and communicates with one of the fluid conducting passages; and first and second balloons carried by the catheter and extending outwardly from the lateral wall, the balloons communicating with respective fluid conducting passages and being disposed so that the fluid outlet passage is located between the balloons, wherein one of the balloons is a high compliance volume balloon and the other of the balloons is a low compliance pressure balloon dimensioned to radially dilate the body passage when expanded by a fluid under pressure.

Objects according to the invention are further achieved by a method for eliminating an obstruction from a body passage having a wall, using the device described above, by:

introducing the catheter into the passage and into proximity to the obstruction;

performing a balloon angioplasty treatment by positioning the low compliance pressure balloon in line with the obstruction, inflating the low compliance pressure balloon to dilate the obstruction, and then deflating the low compliance pressure balloon; and performing a chemical treatment by placing the catheter in a position where the obstruction is situated between the first and second balloons, causing the first and second balloons to at least partially seal a region of the passage containing the obstruction, and introducing a chemical substance into that region and into contact with the obstruction, via the fluid outlet passage, the chemical substance being selected to promote at least one of clot dissolution, prevention of clot formation and repair of the body passage wall.

According to one embodiment of this method, the mechanical widening of a region of an artery is followed by a chemical treatment which inhibits reappearance of a blockage at the location being treated.

According to the invention, a conventional balloon angioplasty operation may be followed by a chemical treatment in which the portion of the blood vessel wall which has been dilated, and thus which is likely to have been torn, is contacted by a treatment agent, such as Hirudin, which inhibits the formation of clot precursors, such as thrombin, thereby preventing the formation of an extracellular matrix which would lead to restenosis. Then, after tears which were created in the artery wall by the angioplasty step have closed sufficiently to prevent seepage through the artery wall, a second chemical agent having the effect of inhibiting proliferation of smooth muscles is introduced into the region being treated. Such chemicals can include ACE inhibitors and drugs which are known for use in cancer therapy. Chemical agents, such as transduced epithelial cells, which form a coating on the artery wall can also be used.

One advantage of the present invention resides in the provision of a catheter device having only two balloons for performing a combination of balloon angioplasty and chemical dissolution, or chemoplasty. Since each balloon employed on a catheter requires a separate inflation fluid lumen, reduction of the total number of balloons, with the attendant reduction in the number of lumens, allows the size of the catheter to be reduced, thereby making the catheter available for use in smaller body passages, and/or permits the diameter of the blood bypass flow lumen to be increased, which enables the catheter to be used in larger blood vessels where a greater volume of blood flow to organs downstream of the catheter device must be provided. Obviously, reduction of the number of lumens provided in a catheter also reduces the cost of manufacturing such catheter.

In addition, the catheter according to the invention allows a balloon angioplasty procedure to be preceded or followed immediately by a chemical treatment of the region which has been dilated, without requiring withdrawal of the catheter and insertion of a different catheter.

BRIEF DESCRIPTION OF THE DRAWING

The FIG. 1 is a cross-sectional view of one embodiment of a catheter device according to the present invention.

DESCRIPTION OF THE PREFERRED EMBODIMENTS

Figure 1:
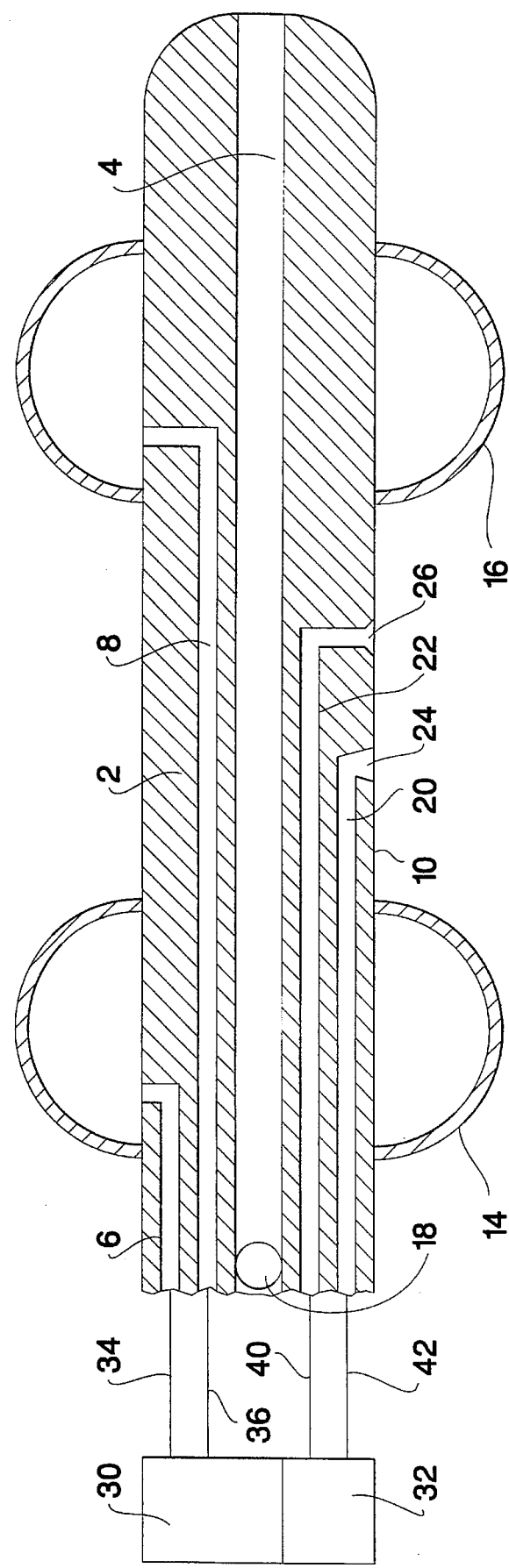

One embodiment of a catheter system which may be employed in the practice of the present invention is illustrated in the Fig. and is preferably constituted by a single catheter 2 provided with a plurality of axial lumens and outlet passages, as will be described below. The Figure shows essentially the distal end of catheter 2, which will be inserted into a body passage to be treated.

The lumens provided in catheter 2 include a central lumen 4 which opens at the distal end of catheter 2 and extends over at least a portion of the length of catheter 2 toward the proximal end thereof. Lumen 4 communicates with a region surrounding catheter 2 via one or more radial passages 18 located between balloon 14 and the proximal end of catheter 2. The function performed by lumen 4 will be described in greater detail below.

Catheter 2 additionally contains two balloon inflation lumens 6 and 8, each having an outlet opening at the peripheral surface 10 of catheter 2. The catheter system further includes two balloons, or cuffs, 14 and 16, each secured to surface 10 and surrounding the outlet opening of a respective one of lumens 6 and 8. Each of balloons 14 and 16 is inflatable to at least block a body passage in which catheter 2 is inserted.

One of the balloons, preferably balloon 14, is a low compliance pressure balloon of the type conventionally employed to perform balloon angioplasty. Such a balloon will, when fluid at a sufficient pressure is supplied thereto, expand with a force sufficient to dilate the portion of the body passage in contact with the balloon.

In contrast, the other balloon, preferably balloon 16, is a high compliance volume balloon which differs from the type of balloon normally employed in angioplasty in that a high compliance volume balloon will, when inflated with a pressure medium, expand into any available space, without applying any significant force to bodies in contact therewith.

Thus, when a low compliance pressure balloon is inflated, it will apply a force to a surface in contact therewith. If such a surface is, for example, a tubular body passage, the effect will be dilation of the body passage. In contrast, if an inflation fluid at the same pressure were introduced into a high compliance volume balloons, that balloon would tend to expand in all directions in which it is not constrained, and would thus not impose significant forces on the wall of a tubular passage.

Preferably, the low compliance pressure balloon is in the form of an annular cuff. The high compliance volume balloon may also be in the form of an annular cuff or may be mounted eccentrically on surface 10 of catheter 2 and constructed to expand both radially and circumferentially in order to seal the region surrounding catheter 2. Such an eccentric balloon is disclosed, for example, in issued U.S. Pat. No. 5,195,955.

Figure 4:
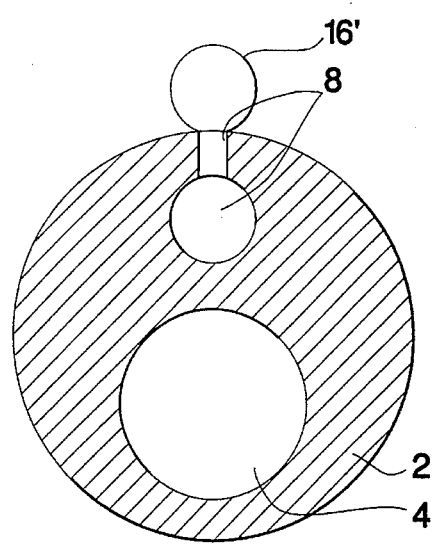
FIG. 4 is a cross-sectional view showing the embodiment of FIG. 2 with its balloon in a deflated state.
Figure 3:
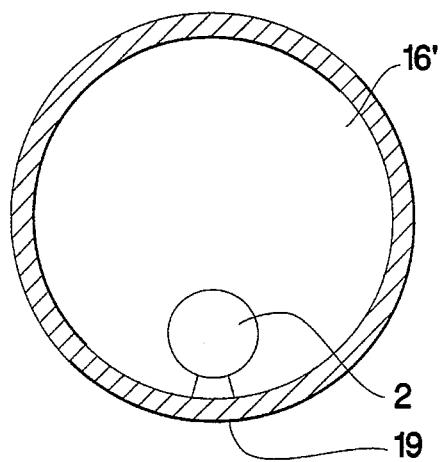
FIG. 3 is a cross-sectional view showing the embodiment of FIG. 2 in an artery.
Figure 2:
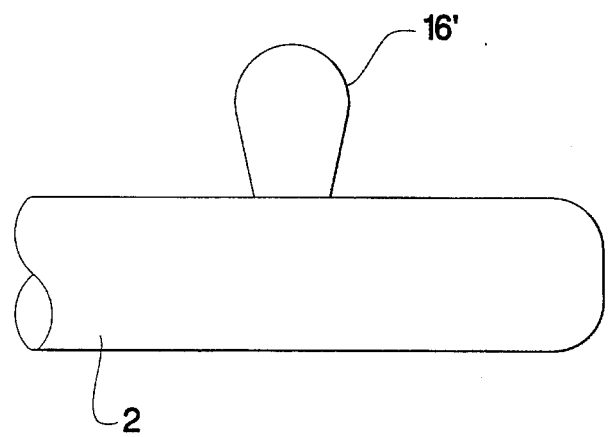
FIG. 2 is a side elevational detail view of a portion of a second embodiment of a catheter device according to the invention.

An embodiment of a catheter device according to the invention provided with such an eccentric balloon is shown in FIGS. 2, 3 and 4. FIG. 2 is an elevational view showing the distal end of catheter 2 provided with an eccentric balloon 16. In FIG. 2, eccentric balloon 16 is deflated.

FIG. 3 is a cross-sectional view, taken in a plane perpendicular to the axis in FIG. 2, showing catheter 2 in an artery 19, with balloon 16' inflated. Finally FIG. 4 is a cross-sectional view, in the same plane as FIG. 3, but to a larger scale, showing balloon 16' deflated.

Catheter 2 further includes two additional lumens 20 and 22 which extend to respective fluid passages 24 and 26 which open at surface 10 of catheter 2.

Lumen 20 and passage 24 may be employed for delivering a chemical substance to a region of a body passage located between balloons 14 and 16, fluid flowing to that region via passage 24.

Lumen 22 and passage 26 are optional components which may be provided in order to effect a suction action while fluid is being delivered via lumen 20 and passage 24. However, in accordance with various embodiments of methods according to the invention, both the delivery of a chemical substance and removal of fluid from the region between balloons 14 and 16 may be performed in alternation via lumen 20 and passage 24.

At the proximal end of catheter 2, outside of the patient's body, there are provided suitable control units 30 and 32. Control unit 30 is connected via respective lines 34 and 36 to lumens 6 and 8 in order to control the inflation of balloons 14 and 16. Unit 32 is connected via respective lines 40 and 42 to lumens 20 and 22 in order to control the delivery of chemical substances to and the removal of fluid from the region of a body passage located between balloons 14 and 16.

Components 30 and 32 may be constructed according to techniques well known in the art for controlling the delivery of appropriate fluids.

In the embodiment illustrated in the Figure, passages 24 and 26 are situated between balloons 14 and 16.

After catheter 2 has been inserted into a body passage, such as a blood vessel, balloons 14 and 16 may be inflated in a manner to block flow of fluid through the passage in an annular region between surface 10 and the passage wall, thereby creating an isolated treatment region. Into that region, a chemical substance for performing a desired treatment may be introduced via lumen 20 and passage 24.

Periodically, the fluid within the isolated region can be withdrawn, via lumen 20 or optional lumen 22, and delivered to unit 32 for purposes of chemical analysis. If the chemical substance being delivered to the isolated region acts to dissolve material, such as plaque, in that region, the dissolved material may be optionally withdrawn via catheter 22 and passage 26.

When catheter 2 is so installed and balloons 14 and 16 are inflated to create the above-described isolated region, it is nevertheless essential that some flow of blood be maintained between regions of the blood vessel located upstream and downstream of the isolated region. The purpose of lumen 4 and one or more passages 18 is to allow such blood flow to be maintained. In addition, if it is desired to introduce catheter 2 into a body passage with the aid of a guide wire, which is a conventional technique in the art, lumen 4 may extend to the proximal end of catheter 2 and serve as the guide wire passage.

In accordance with the invention, the device shown in the Figure can be employed in the following manner.

Firstly, with balloons 14 and 16 deflated, catheter 2 is inserted, via its distal end (the right-hand end in the Figure) into a body passage. If the body passage is a blood vessel, insertion can be performed angiographically, as described in U.S. Pat. No. 5,090,960.

If catheter 2 is inserted for the purpose of performing balloon angioplasty on an obstruction in a blood vessel, insertion is performed to bring pressure balloon 14 into alignment with the obstruction, or with a portion of the obstruction. Positioning of balloon 14 relative to the obstruction can be performed according to any of the conventional techniques utilized in balloon angioplasty.

Balloon 14 may then be inflated in order to effect an angioplasty treatment, i.e. to dilate the portion of the blood vessel containing the obstruction and balloon 14 is maintained inflated for an appropriate period of time.

The present invention can prove particularly beneficial for treating a patient suffering from a severe arterial blockage constituted by plaque. Since there is presently no product which can chemically dissolve plaque, such a blockage can be alleviated most quickly by balloon angioplasty. However, angioplasty frequently produces several undesired effects, namely tearing of the blood vessel wall and initiation of clots or tissue growth which result in acute reclosure of the blood vessel. Reclosure occurs in 13% of angioplasty patients not previously treated with thrombolytic drugs and in 30–40% of patients who had been treated with thrombolytic drugs prior to angioplasty.

More specifically, after a blood vessel wall has been torn by an angioplasty procedure, there will occur, in the absence of preventive treatment, cell proliferation and clot formation processes, which are interdependent. Clot formation is preceded by the formation of thrombin, which induces formation of smooth cells; smooth muscle cell proliferation triggers formation of an extracellular matrix. These are all part of the body's normal reaction to blood vessel wall tearing.

In addition, a blockage may consist of a blood clot along with plaque.

According to the invention, angioplasty may be followed by a treatment with thrombolytic (clot dissolving) drugs, and/or other agents, to be described below, to help to prevent acute reclosure of the artery.

To prepare for these treatments with drugs or other agents, balloon 14 is at least partially is deflated and, according to the invention, catheter 2 is retracted slightly, to the left in the Figure, in order to bring the region containing the obstruction that was dilated to a location between, or straddled by, balloons 14 and 16. Then, balloon 16 may be inflated to block the blood vessel without imposing any significant radial force thereon. At this time, balloon 14 can also be inflated by supplying, via line 34, an inflation fluid at a significantly lower pressure than that which was employed to perform angioplasty. By way of example, for a typical angioplasty balloon, the lower pressure can be of the order of 1–2 atmospheres, whereas the pressure employed during angioplasty can be of the order of 10–15 atmospheres. The application of a lower pressure will cause balloon 14 to serve as a blocking balloon without acting to dilate the blood vessel wall. The pressure applied to balloon 14 can be readily controlled by suitable control means in unit 30.

Then a chemical treatment can be performed on the region which was previously subjected to balloon angioplasty. This chemical treatment may be a thrombolytic treatment in which a clot dissolution agent, such as Hirudin (TM), is delivered to the isolated treatment region between balloons 14 and 16 via lumen 20 and passage 24. If desired, dissolved clot material can be removed via lumen 22 and passage 26.

Because the treatment region is isolated from the rest of the circulatory system, conventional thrombolytic drugs may be administered via lumen 20 and passage 24 in a higher concentration than heretofore possible and can effect substantially complete clot dissolution over a period of five to ten minutes.

During the dissolution process, fluid samples are withdrawn periodically via lumen 20 and passage 24, or via lumen 22 and passage 26, and are analyzed to identify certain products, such as fibrin split products and other chemical products known to be indicative of total clot dissolution. The samples are further analyzed to determine the relative concentrations of blood and treatment agents in the isolated treatment regions and the rate of delivery of treatment agents is adjusted accordingly. The withdrawal of fluid samples for purposes of analysis, i.e. for purposes of monitoring, can be effected via either lumen 20 or lumen 22 in the manner described in U.S. Pat. No. 5,222,941.

After it has been determined that the clot has been dissolved, the extent of remaining artery blockage is determined, possibly by radiography aided by injection of radiographic dyes. If the remaining blockage is small, and biological parameters being monitored indicate that clot will not recur, balloons 14 and 16 can be deflated and a heparin drip is simultaneously started. Catheter 2 is left in place until the possibility of clot recurrence can be ruled out, and balloons 14 and 16 can be periodically reinflated, only to the extent of blocking the artery, to permit withdrawal of samples from the treatment region, which samples are analyzed to allow a determination of the probability of clot recurrence.

As an alternative, or in addition, to the delivery of a chemical dissolution agent, the conventional balloon angioplasty operation can be followed by a chemical treatment in which the portion of the blood vessel wall which has been dilated, and thus which is likely to have been torn, is treated to prevent clot formation and reformation and to promote repair and healing of the torn tissue in a manner that inhibits development of smooth muscle tissue that would create a new blockage.

For the above mentioned chemical treatment distinct from clot dissolution, various agents are introduced into the isolated treatment region via lumen 20 and passage 24. These agents and their purpose will be described below.

In order to interrupt formation of clot precursor, or thrombin, and prevent smooth muscle proliferation, use can be made of Angiotension Converting Enzyme (ACE) inhibitors, such as enalpril, and/or anti-neoplastic, anti-proliferation cancer drugs, such as methotrexate. These agents are maintained in the treatment region while fluid in the region is sampled. These samples are subjected to immuno-chemical analysis of clot and preclot components and analysis to monitor the presence of specific tissue growth hormones. Clot precursors can be monitored by analyzing fibrin split products. The absence, or a sufficiently low level of, clot and preclot components, specific tissue growth hormones and fibrin split products will indicate that treatment with the above agents can be terminated.

At the same time, the closing of tears in the inner lining of the blood vessel can be promoted by delivering transduced epithelial cells to the treatment region. Transduced epithelial cells are epithelial cells which have been altered, prior to introduction into the treatment region, to alter their genetic code. This can be done, for example, by treatment of the cells with a retrovirus, by electroporation, or by alteration of cell lysosomes. Techniques of this type are known.

The transduced epithelial cells will be introduced into the treatment region to become attached, or seeded, to the blood vessel wall. They will then propagate to close tears. This treatment is monitored by fluorescent techniques on the basis of the fact that seeded transduced epithelial cells will fluoresce.

As an example of a procedure according to the invention, a patient presents symptoms of blockage of an artery by a thrombus, or blood clot. The patient could first be treated by conventional intravenous administration of thrombolytic drugs. If, after an appropriate period of time it is judged that the blockage has not been sufficiently alleviated, the location of the blockage is identified angiographically and a device according to the invention is inserted into the affected artery. This insertion may be done with the aid of a guide wire inserted through central lumen 4. Catheter 2 is then advanced along the guide wire until balloons 14 and 16 straddle the obstruction. Balloons 14 and 16 are inflated only to the extent needed to block the artery and create the isolated treatment region. During this time, blood is permitted to flow past the obstruction via lumen 4 and passages 18. A thrombolytic drug is then introduced into the isolated treatment region, via catheter 2, as described above, and the progress of the dissolution process is monitored, also as described above.

However, it will frequently occur that upon completion of chemical thrombolysis, a substantial, life-threatening blockage remains. In this case, it may be indicated that balloon angioplasty is essential to patient survival. In this case, catheter 2 will be advanced a short distance, to bring balloon 14 in line with the blockage, and balloon 14 is inflated to a greater extent than in the thrombolytic procedure described above to open the artery.

Thereafter, treatments to dissolve clot, prevent clot and smooth muscle cell formation and repair vessel wall tears will be performed, as described above.

In the procedure described above, the composition of the fluid in the treatment region can be monitored in the same manner as that described earlier herein with respect to chemical dissolution treatments.

If all fluid flow to and from the isolated region, including the delivery of a chemical substance, the withdrawal of fluid samples for analysis and the removal of dissolved material are performed via lumen 20 and passage 24, catheter 2 need not be provided with lumen 22 and passage 26. In that case, the fabrication of catheter 2 will be simplified and catheter 2 can be given a smaller diameter and/or blood bypass flow lumen can be given a larger diameter to assure adequate blood flow to organs downstream of the region being treated.

With the device according to the invention, balloon angioplasty can be performed, before or after chemical thrombolytic treatment, followed by deflation of the angioplasty balloon to permit blood flow to resume, thereby alleviating severe patient distress. In addition, both balloons can be inflated so as to not dilate the blood vessel and a chemical treatment can be performed to effect at least one of clot dissolution, clot reformation and artery wall treatment as described earlier herein.

A catheter according to the invention may also be employed in conjunction with a known device for disintegrating plaque and clot by application of energy, such as laser radiation or ultrasonic vibrations, or by a mechanical cutting action. One device of this type is disclosed in U.S. Patent No. 4,870,953.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A device for treating conditions causing obstructions in a body passage, consisting of:

a catheter dimensioned to be insertable into the body passage and having a lateral wall and a distal end via which said catheter can be inserted into the body passage, said catheter being provided internally with fluid conducting passages and further being provided with a fluid outlet passage which extends through said lateral wall and communicates with one of said fluid conducting passages; and first and second balloons carried by said catheter and extending outwardly from said lateral wall, said balloons communicating with respective fluid conducting passages and being disposed so that said fluid outlet passage is located between said balloons, wherein one of said balloons is a high compliance volume balloon and the other of said balloons is a low compliance pressure balloon dimensioned to radially dilate the body passage when expanded by a fluid under pressure.

2. A device as defined in claim 1 wherein said first balloon is said high compliance volume balloon and is located between said distal end of said catheter and said outlet passage.

3. A device as defined in claim 1 wherein said high compliance volume balloon is an eccentric balloon.

4. A method for eliminating an obstruction from a body passage having a wall, using the device of claim 1, comprising:

introducing the catheter into the passage and into proximity to the obstruction;

performing a balloon angioplasty treatment by positioning the low compliance pressure balloon in line with the obstruction, inflating the low compliance pressure balloon to dilate the obstruction, and then deflating the low compliance pressure balloon; and performing a chemical treatment by placing the catheter in a position where the obstruction is situated between the first and second balloons, causing the first and second balloons to at least partially seal a region of the passage containing the obstruction, and introducing a chemical substance into that region and into contact with the obstruction, via the fluid outlet passage, the chemical substance being selected to promote at least one of clot dissolution, prevention of clot formation and repair of the body passage wall.

5. A method as defined in claim 4 wherein said step of inflating the low compliance pressure balloon comprises establishing a first pressure within the pressure balloon, and said step of causing the first and second balloons to at least partially seal a region of the passage comprises establishing a second pressure, which is lower than the first pressure, within the pressure balloon.

6. A method as defined in claim 5 wherein said step of causing the first and second balloons to at least partially seal a region of the passage comprises inflating the volume balloon at any time after initiation of said introducing step.

7. A method as defined in claim 4 wherein the high compliance volume balloon is located between the distal end of the catheter and the outlet passage.

8. A method as defined in claim 4 wherein said step of causing the first and second balloons to at least partially seal a region of the passage comprises inflating the volume balloon at any time after initiation of said introducing step.

9. A method as defined in claim 4 wherein, during such step of performing a balloon angioplasty treatment, the catheter is in a first position relative to the body passage, and the operation of placing the catheter during said step of performing a chemical treatment comprises moving the catheter relative to the body passage, from the first position to a second position.

* * * * *